United States Patent
Wang

(10) Patent No.: US 12,409,340 B2
(45) Date of Patent: Sep. 9, 2025

(54) SYSTEM AND METHOD FOR RADIATION THERAPY AND IMMOBILIZING DEVICE THEREOF

(71) Applicant: SHANGHAI UNITED IMAGING HEALTHCARE CO., LTD., Shanghai (CN)

(72) Inventor: Xukun Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1127 days.

(21) Appl. No.: 17/128,235

(22) Filed: Dec. 21, 2020

(65) Prior Publication Data
US 2021/0128943 A1   May 6, 2021

Related U.S. Application Data

(63) Continuation of application No. PCT/CN2019/111745, filed on Oct. 17, 2019.

(51) Int. Cl.
*A61N 5/10*   (2006.01)
*A61F 7/00*   (2006.01)
(Continued)

(52) U.S. Cl.
CPC .............. *A61N 5/10* (2013.01); *A61F 7/00* (2013.01); *A61G 13/1275* (2013.01); *G06N 5/02* (2013.01);
(Continued)

(58) Field of Classification Search
CPC .... A61N 5/10; A61N 5/1001; A61N 2005/10; A61N 2005/1048; A61N 2005/1049;
(Continued)

(56) References Cited

U.S. PATENT DOCUMENTS

| | | | |
|---|---|---|---|
| 6,511,475 B1* | 1/2003 | Altshuler | A61B 18/203 606/2 |
| 2009/0000614 A1* | 1/2009 | Carrano | A61G 13/12 128/118.1 |

(Continued)

FOREIGN PATENT DOCUMENTS

| | | |
|---|---|---|
| CN | 206482800 U | 9/2017 |
| CN | 108744317 A | 11/2018 |
| CN | 208865064 U | 5/2019 |

OTHER PUBLICATIONS

International Search Report in PCT/CN2019/111745 mailed on Jul. 15, 2020, 4 pages.

(Continued)

*Primary Examiner* — Alireza Nia
*Assistant Examiner* — Gina McCarthy
(74) *Attorney, Agent, or Firm* — METIS IP LLC

(57) ABSTRACT

A radiation therapy system may be provided. The system may include a therapeutic apparatus. The therapeutic apparatus may include a radiation source for directing therapeutic radiation to at least one portion of a region of interest (ROI) of a subject, and an immobilizing device for immobilizing the subject. The system may obtain characteristics information of the subject. The system may preheat the immobilizing device according to a predictive model that processes the characteristics information of the subject. The system may send a control signal to the therapeutic apparatus for applying the therapeutic radiation to the at least one portion of the ROI immobilized by the preheated immobilizing device when the immobilizing device is preheated to a certain temperature.

18 Claims, 11 Drawing Sheets

(51) Int. Cl.
  *A61G 13/12* (2006.01)
  *G06N 5/02* (2023.01)
  *G06N 20/00* (2019.01)
  *G16H 20/40* (2018.01)
  *H05B 1/02* (2006.01)

(52) U.S. Cl.
  CPC ............ *G06N 20/00* (2019.01); *G16H 20/40* (2018.01); *H05B 1/025* (2013.01); *A61F 2007/0096* (2013.01); *A61N 2005/1055* (2013.01); *A61N 2005/1061* (2013.01); *A61N 2005/1074* (2013.01); *A61N 2005/1097* (2013.01)

(58) Field of Classification Search
  CPC .... A61N 2005/1055; A61N 2005/1061; A61N 2005/1074; A61N 2005/1097; A61F 5/37; A61F 5/3761; A61F 5/369; A61F 2007/0091; A61F 2007/0096; A61G 7/10; A61G 7/1001; A61G 7/1013; A61G 7/1073; A61G 13/02; A61G 12/1265; A61G 12/1275; G06N 5/00; G06N 5/02; H05B 1/02; H05B 1/0227; H05B 1/025; G16H 20/40
  USPC .............................................. 5/630; 128/870
  See application file for complete search history.

(56) References Cited

U.S. PATENT DOCUMENTS

| | | |
|---|---|---|
| 2009/0319009 A1 | 12/2009 | Koch et al. |
| 2012/0279953 A1* | 11/2012 | Augustine ................ A61F 7/08 219/217 |
| 2013/0066135 A1* | 3/2013 | Rosa ........................ A61N 5/10 600/1 |
| 2016/0213337 A1* | 7/2016 | Coppens .................. A61N 5/10 |
| 2016/0378948 A1* | 12/2016 | Kuusela .................. G06N 5/00 703/11 |
| 2018/0133518 A1 | 5/2018 | Harper et al. |
| 2019/0201268 A1 | 7/2019 | Sayadi et al. |
| 2020/0086996 A1* | 3/2020 | La Montagna .... B64D 11/0626 |
| 2020/0093445 A1* | 3/2020 | DeFreitas ............. A61B 6/045 |
| 2022/0007084 A1* | 1/2022 | Aytekin ............... H04N 21/845 |
| 2022/0091837 A1* | 3/2022 | Chai ....................... G06F 8/36 |

OTHER PUBLICATIONS

Written Opinion in PCT/CN2019/111745 mailed on Jul. 17, 2020, 4 pages.

First Office Action in Chinese Application No. 201980038971.6 mailed on Jul. 19, 2022, 21 pages.

* cited by examiner

800

```
802 Obtaining, from a database, a set of training data
including labeled historical preheating data of immobilizing
components corresponding to a plurality of subjects and
the characteristics of the plurality of subjects 804 Obtaining an initial model 806 Training the initial model based on the training data 808 Updating parameters of the initial model by minimizing a
loss function of the initial model 810 Determining a predictive model
```

FIG. 8

SYSTEM AND METHOD FOR RADIATION THERAPY AND IMMOBILIZING DEVICE THEREOF

CROSS-REFERENCE TO RELATED APPLICATIONS

This application is a continuation of Interactional Application No. PCT/CN2019/111745, filed on Oct. 17, 2019, the contents of which are hereby incorporated by reference.

TECHNICAL FIELD

The present disclosure generally relates to a radiation therapy system, and more particularly, relates to an image-guided radiation therapy system including a heated immobilizing device.

BACKGROUND

Nowadays, a radiation therapy is an effective means for diagnosing and treating a tumor. A radiation therapy system/apparatus, such as an image-guided radiotherapy (IGRT) system, may be used to perform the radiation therapy. In some cases, one or more components of the radiation therapy apparatus (e.g., a linear accelerator) may work normally at a relatively low-temperature in low-humidity environment. Thus, the temperature in a treatment room may be at about 20 degrees Celsius, even much lower. The low-temperature is not a friendly environment for the patients to receive radiation therapy, as most of those patients have tumors and are weak. Moreover, during the treatment time that the patients receive the radiation therapy, they usually have to take off their clothes and lie on an immobilizing device (e.g., a vacuum cushion) in order to be secured. The patients may feel cold and uncomfortable in the low-temperature treatment environment for a long treatment time. Some patients may tremble due to the low temperature. As a result, the radiation therapy apparatus may not accurately shoot therapeutic radiation to a treatment region (e.g., the tumor region), rendering a poor therapeutic effect. Therefore, it is desirable to provide a radiation therapy system having a high therapeutic quality with a comfortable treatment environment as well.

SUMMARY

In a first aspect of the present disclosure, a radiation therapy (RT) system is provided. The RT system may include a therapeutic apparatus, at least one storage device storing executable instructions, and at least one processing device in communication with the therapeutic apparatus and the at least one storage device. The therapeutic apparatus may include a radiation source for directing therapeutic radiation to at least one portion of a region of interest (ROI) of a subject, and an immobilizing device for immobilizing the subject. When executing the executable instructions, the at least one processing device may cause the system to perform one or more operations as following. The system may obtain characteristics information of the subject. The system may preheat the immobilizing device according to a predictive model that processes the characteristics information of the subject. The system may send a control signal to the therapeutic apparatus for applying the therapeutic radiation to the at least one portion of the ROI immobilized by the preheated immobilizing device when the immobilizing device is preheated to a certain temperature.

In some embodiments, the therapeutic apparatus may further include a supporting platform, and the preheated immobilizing device may be operably connected to the supporting platform.

In some embodiments, the immobilizing device may include a vacuum cushion. The vacuum cushion may include a shell installed with a valve that is connectable to a vacuum source, a heating element attached to an inner side of the shell, an electrical circuit electrically connected to the heating element and a filler material contained within a region defined by the shell. The electrical circuit may supply a heating voltage to the heating element for preheating the vacuum cushion.

In some embodiments, the heating element may include a flexible heating film that does not interfere a radiation dose that the subject receives.

In some embodiments, the flexible heating film may include a Carbon fiber heating film.

In some embodiments, the flexible heating film may include a Graphene heating film.

In some embodiments, the immobilizing device may further include a temperature sensor for detecting a heating temperature of the vacuum cushion.

In some embodiments, the electrical circuit may be connected to a temperature controller for control of the heating temperature of the vacuum cushion. The temperature controller may have a temperature memory function for recording a previously configured preferable temperature for the subject, and directly configure the recorded preferable temperature as the heating temperature of the vacuum cushion.

In some embodiments, the system may generate, based on historical preheating data of the immobilizing devices corresponding to a plurality of subjects and the characteristics of the plurality of subjects, the predictive model by training an initial model.

In some embodiments, the system may obtain, from a database, a set of training data. The set of training data may include labeled historical preheating data of the immobilizing components corresponding to a plurality of subjects and the characteristics of the plurality of subjects. The system may train the initial model based on the training data. The training may include updating parameters of the initial model by minimizing a loss function of the initial model and determining the predictive model if the value of the loss function is less than or equal to a threshold.

In some embodiments, the predictive model may include a convolutional neural network (CNN) model.

In some embodiments, the therapeutic apparatus may further include an imaging device configured to acquire image data with respect to the ROI.

In some embodiments, the system may reconstruct an image regarding the at least one portion of the ROI based on the acquired image data. The system may determine a parameter associated with a size of the at least one portion of the ROI based on the reconstructed image. The system may generate the control signal according to the parameter associated with the size of the at the at least one portion of the ROI.

In a second aspect of the present disclosure, a therapeutic apparatus is provided. The therapeutic apparatus may include an imaging device configured to acquire image data with respect to a region of interest (ROI) of a subject, a radiation therapy device configured to apply therapeutic radiation to at least one portion of the ROI in response to a control signal, and an immobilizing device configured to immobilize the at least one portion of the ROI. The immobilizing device may be preheated to a certain temperature before the therapeutic radiation.

In a third aspect of the present disclosure, an immobilizing device is provided. The immobilizing device may include a vacuum cushion. The vacuum cushion may include a shell installed with a valve that is connectable to a vacuum source, a heating element attached to an inner side of the shell, an electrical circuit electrically connected to the heating element and a filler material contained within a region defined by the shell. The electrical circuit may supply a heating voltage to the heating element for preheating the vacuum cushion.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 8 is a flowchart illustrating an exemplary process for generating a predictive model according to some embodiments of the present disclosure.

DETAILED DESCRIPTION

Figure 1:
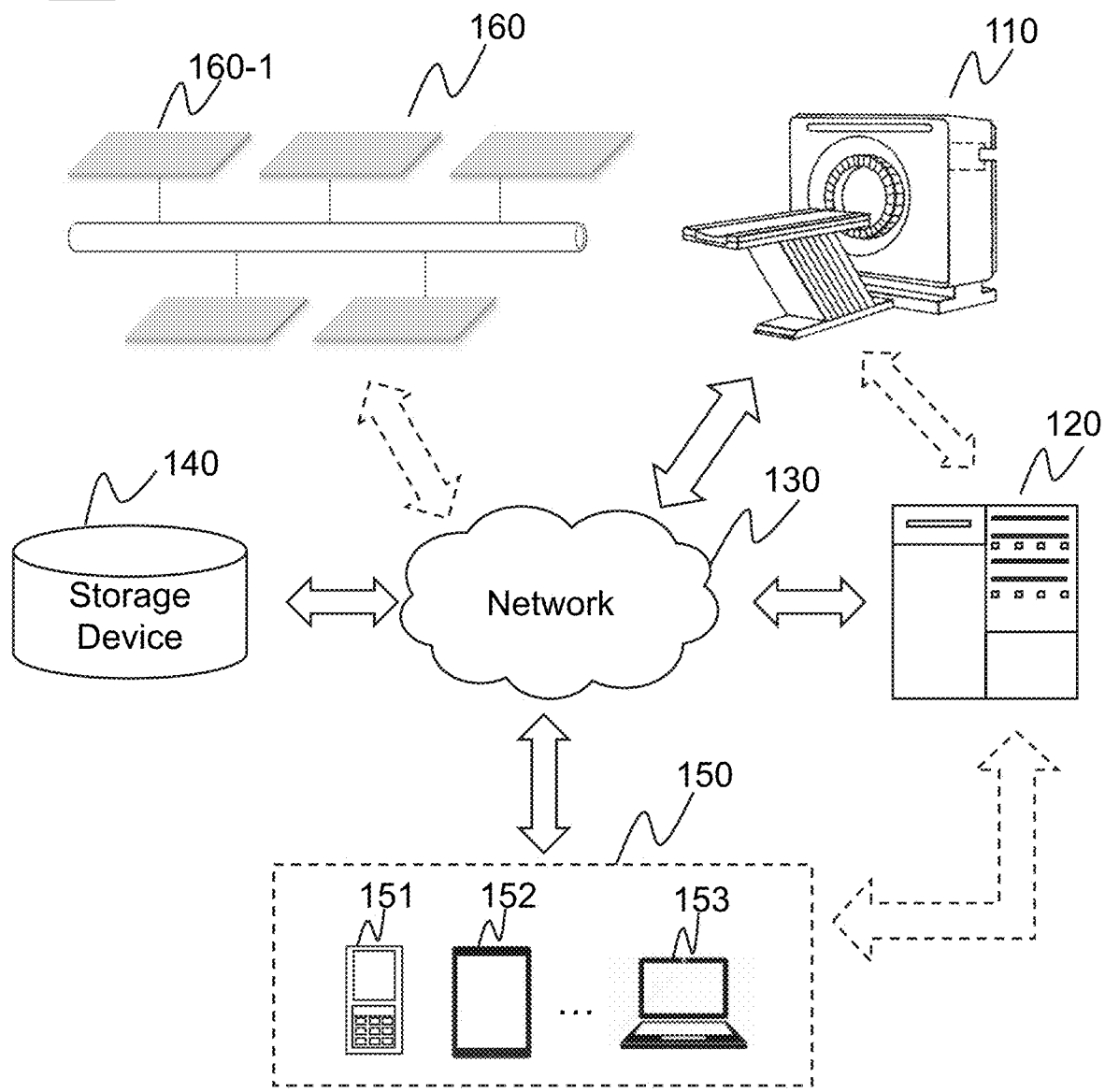
FIG. 1 is a schematic diagram illustrating an exemplary radiation therapy system according to some embodiments of the present disclosure.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Various embodiments of the present disclosure are provided as a radiation therapy system configured to apply therapeutic radiation to at least one portion of region of interest (ROI) of a subject accurately in a comfortable treating environment. In some embodiments, the radiation therapy system may include a therapeutic apparatus for applying the therapeutic radiation. The therapeutic apparatus may include a heatable immobilizing device (e.g., a vacuum cushion) for providing suitable temperature for the subject during the radiation therapy treatment. In some embodiments, the heatable immobilizing device may be preheated by a preheating system before the radiation therapy treatment. In some embodiments, the preheating system or the therapeutic radiation may be preheated according to a predictive model (e.g., a trained CNN model). The predictive model may be used to determine a recommended preheating temperature. In some embodiments, a user (e.g., the subject or a technician) may configure a preferable preheating temperature for the subject through a temperature controller of the immobilizing device. The immobilizing device may be preheated to the configured preheating temperature. The heated immobilizing device may be disposed on a treatment table of the therapeutic apparatus. The subject may feel warm and comfortable when the subject lies on the heated immobilizing device during the radiation therapy treatment. In some cases, the body tremble caused by the low temperature may be avoided, and the therapeutic radiation may be accurately applied as well.

FIG. 1 is a schematic diagram illustrating an exemplary radiation therapy system according to some embodiments of the present disclosure. In some embodiments, radiation therapy system 100 may be a multi-modality medical imaging system including, for example, an image-guide radiotherapy (IGRT) system (e.g., a positron emission tomography-radiotherapy (PET-RT) system, a magnetic resonance imaging-radiotherapy (MRI-RT) system, etc.) For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, a processing device 120, a network 130, a storage device 140, and one or more terminal devices 150. In some embodiments, the radiation therapy system 100 may further include a system 160 for preheating one or more immobilizing devices (e.g., an immobilizing device 160-1) used by one or more subjects (e.g., patients). Each subject may have his/her own immobilizing device. In some embodiments, the immobilizing device may be configured to suit the subject's needs (e.g., the subject's therapeutic apparatus or corresponding treatment plan). Hereinafter the system 160 is referred to as the preheating system 160. In some embodiments, the therapeutic apparatus 110, the processing device 120, the storage device 140, the terminal device 150 and/or the preheating system 160 may be connected to and/or communicate with each other via a wireless connection (e.g., the wireless connection provided by the network 130), a wired connection (e.g., the wired connection provided by the network 130), or any combination thereof.

The therapeutic apparatus 110 may include an imaging component (or an imaging device). For example, the imaging component may include a PET scanner, a CT scanner, an MRI scanner, or the like, or any combination thereof. Taking the MRI scanner as an example, the MRI scanner may generate image data associated with magnetic resonance signals (hereinafter referred to as "MRI signals") via scanning a subject or a part of the subject. As used herein, a subject may correspond to a user, a patient, or an object. In some embodiments, the subject may include a body, a substance, an object, or the like, or any combination thereof. In some embodiments, the subject may include a specific portion of a body, a specific organ, or a specific tissue, such as head, brain, neck, body, shoulder, arm, thorax, heart, stomach, blood vessel, soft tissue, knee, feet, or the like, or any combination thereof. In some embodiments, the therapeutic apparatus 110 may transmit the image data via the network 130 to the processing device 120, the storage device 140, and/or the terminal device 150 for further processing. For example, the image data may be sent to the processing device 120 for generating an MRI image, or may be stored in the storage device 140.

The therapeutic apparatus 110 may also include a radiation therapy component (hereinafter referred to as "radiation therapy device"). The radiation therapy device may provide radiation for target region (e.g., a tumor) treatment. The radiation used herein may include a particle ray, a photon ray, etc. The particle ray may include neutron, proton, electron, p-meson, heavy ion, α-ray, or the like, or any combination thereof. The photon ray may include X-ray, γ-ray, ultraviolet, laser, or the like, or any combination thereof. For illustration purposes, a radiation therapy device associated with X-ray may be described as an example. In some embodiments, the therapeutic apparatus 110 may generate a certain dose of X-rays to perform radiotherapy under the assistance of the image data provided by the imaging device, such as the MRI scanner. For example, the image data may be processed to locate a tumor and/or determine the dose of X-rays.

The processing device 120 may process data and/or information obtained from the therapeutic apparatus 110, the storage device 140, the terminal device 150, and/or the preheating system 160. For example, the processing device 120 may process image data and reconstruct at least one MRI image based on the image data. As another example, the processing device 120 may determine the position of the treatment region and the dose of radiation based on the at least one MRI image. The MRI image may provide advantages including, for example, superior soft-tissue contrast, high resolution, geometric accuracy, which may allow accurate positioning of the treatment region. The MRI image may be used to detect a change of the treatment region (e.g., a tumor regression or metastasis) between when the treatment plan is determined and when the treatment is carried out, such that an original treatment plan may be adjusted accordingly. The original treatment plan may be determined before the treatment commences. For instance, the original treatment plan may be determined at least one day, or three days, or a week, or two weeks, or a month, etc., before the treatment commences.

In the original or adjusted treatment plan, the dose of radiation may be determined according to, for example, synthetic electron density information. In some embodiments, the synthetic electron density information may be generated based on the generated image (e.g., the MRI image).

In some embodiments, the processing device 120 may be a single processing device that communicates with and process data from the imaging device (e.g., the MRI device) and/or the radiation therapy device of the therapeutic apparatus 110. Alternatively, the processing device 120 may include at least two processing devices. One of the at least two processing devices may communicate with and process data from the imaging device of the therapeutic apparatus 110, and another one of the at least two processing devices may communicate with and process data from the radiation therapy device of the therapeutic apparatus 110. In some embodiments, the processing device 120 may include a treatment planning system. The at least two processing devices may communicate with each other. In some embodiments, the processing device 120 may be used to perform one or more preheating operations for the immobilizing device through the preheating system 160 or the therapeutic apparatus 110.

In some embodiments, the processing device 120 may be a single server or a server group. The server group may be centralized or distributed. In some embodiments, the processing device 120 may be local to or remote from the therapeutic apparatus 110. For example, the processing device 120 may access information and/or data from the therapeutic apparatus 110, the storage device 140, the terminal device 150 and/or the preheating system 160 via the network 130. As another example, the processing device 120 may be directly connected to the therapeutic apparatus 110 as illustrated by the bidirectional arrow in dotted lines connection the processing device 120 and the therapeutic apparatus 110 in FIG. 1, the terminal device 150 as illustrated by the bidirectional arrow in dotted lines connection the processing device 120 and the terminal device 150 in FIG. 1, the storage device 140 and/or the preheating system 160 to access information and/or data. In some embodiments, the processing device 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the processing device 120, the storage device 140, the terminal device 150, or the preheating system 160) may communicate information and/or data with one or more other components of the radiation therapy system 100 via the network 130. For example, the processing device 120 may obtain image data from the therapeutic apparatus 110 via the network 130. As another example, the processing device 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the processing device 120 and/or the terminal device 150. In some embodiments, the storage device 140 may store data and/or instructions that the processing device 120 may execute or use to perform exemplary methods described in the present disclosure. In some embodiments, the storage device 140 may include a mass storage device, a removable storage device, a cloud based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the processing device 120 or the terminal device 150). One or more components of the radiation therapy system 100 may access the data or instructions stored in the storage device 140 via the network 130. In some embodiments, the storage device 140 may be part of the processing device 120.

The terminal device 150 may be connected to and/or communicate with the therapeutic apparatus 110, the processing device 120, the storage device 140, and/or the preheating system 160. For example, the processing device 120 may acquire a scanning protocol from the terminal device 150. As another example, the terminal device 150 may obtain image data from the therapeutic apparatus 110 and/or the storage device 140. As a further example, the terminal device 150 may send a preheating request to the preheating system 160. In some embodiments, the terminal device 150 may include a mobile device 151, a tablet computer 152, a laptop computer 153, or the like, or any combination thereof. For example, the mobile device 151 may include a mobile phone, a personal digital assistance (PDA), a gaming device, a navigation device, a point of sale (POS) device, a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the processing device 120.

The preheating system 160 may be configured to preheat one or more immobilizing devices (e.g., the immobilizing device 160-1) correspond to one or more subjects to be treated. The immobilizing device may one-to-one correspond to the subject. The immobilizing device may be a heatable immobilizing device, for example, a vacuum cushion with a heating function. The immobilizing device may be used to position or immobilize a subject or placed at a part of a subject for the treatment or the medical imaging. More descriptions of the immobilizing device may be found elsewhere in the present disclosure (e.g., FIGS. 5A-5B, and the descriptions thereof.). The immobilizing device may be preheated to a suitable temperature for the subject, such as 25 degrees Celsius. During the treatment, when the subject (e.g., a patient) lies on the top of the preheated immobilizing device, he/she will feel comfortable in a relatively low-temperature treatment environment. In some embodiments, the preheating system 160 may provide a plurality of heating interfaces for electrically heating the immobilizing device (e.g., a heating film inside the immobilizing device). For example, the heating interface may include a socket, a plug, a wireless charging interface, or the like, or any combination thereof. The heating interface may be electrically connected to a power generator or a power source.

In some embodiments, the preheating system 160 may preheat the immobilizing device in response to a request for heating the immobilizing device in advance from a subject (or a user). As used herein, the request for heating or preheating the immobilizing device may be referred to as the preheating request or the heating request. The terms "preheating" and "heating" are intended to increase a temperature, and they are used interchangeably in the present disclosure. In some cases, available therapeutic apparatuses in a hospital may be not enough for a huge number of patients at the same time. It may take much time for the patients to wait for the radiation therapy treatment, for example, queue up for the treatment. Moreover, the preheating of their own immobilizing device may cost a certain time. The whole treatment time may be prolonged, resulting in a poor treatment experience and a low treatment effect. In some embodiments, the preheating system 160 may be designed to resolve the issue described above. For example, the preheating system 160 may be used to preheat the immobilizing devices in advance in response to the preheating requests from the patients. They may not need to queue up to preheat the immobilizing devices. When it is his/her turn to receive the radiation therapy treatment, the technician may mount the preheated immobilizing device to the therapeutic apparatus directly. The treatment time for the patient may be shortened, and the treatment efficiency may be improved to some extents.

Merely for illustration, a subject may send a preheating request to the preheating system 160 via an application installed in the mobile device 150-1. Upon receipt of the preheating request, the preheating system 160 may preheat the immobilizing device of the patient. In some embodiments, the immobilizing device may be electrically connected to the preheating system 160 before the preheating. In some embodiments, the preheating system 160 may preheat the immobilizing device according to one or more preheating parameters from the processing device 120. The preheating parameters may include a heating temperature, a preheating start time, a preheating end time, a heating electrical voltage, a heating electrical current, or the like, or any combination thereof. In some embodiments, the one or more preheating parameters may be configured by a temperature controller (e.g., a temperature controller 530 shown in FIG. 5A). In some embodiments, the one or more preheating parameters may be determined based on a predictive model. For example, the predictive model may be invoked by the preheating system 160, and output a recommended heating temperature for the subject. The recommended heating temperature may be a preferable temperature for the subject.

In some embodiments, the preheating system 160 may be connected to and/or communicate with the therapeutic apparatus 110, the processing devices 120, the storage device 140, and/or the terminal device 150. For example, the preheating system 160 may preheat the immobilizing device in response to one or more commands from the processing device 120. The one or more commands may include the one or more preheating parameters determined by the processing device 120. As another example, the preheating system 160 may receive one or more preheating requests sent by the terminal device(s) 150. The preheating request may include characteristics information of the subject, an identifier regarding the immobilizing device, and so on. In some embodiments, the preheating system 160 may be separated from the therapeutic apparatus 110. For example, one or more components of the preheating system 160 (e.g., the heating interfaces, or the power source) may be arranged in a single room separated from the treatment room where the therapeutic apparatus 110 is. In some embodiments, the preheating system 160 may be integrated to the therapeutic apparatus 110. In other words, the immobilizing device may be directly preheated by the therapeutic apparatus 110. In some embodiments, the therapeutic apparatus 110 may include one or more components for preheating the immobilizing device.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. As another example, the processing device 120 may be integrated into the therapeutic apparatus 110, or the preheating system 160. However, those variations and modifications do not depart the scope of the present disclosure.

Figure 2A:
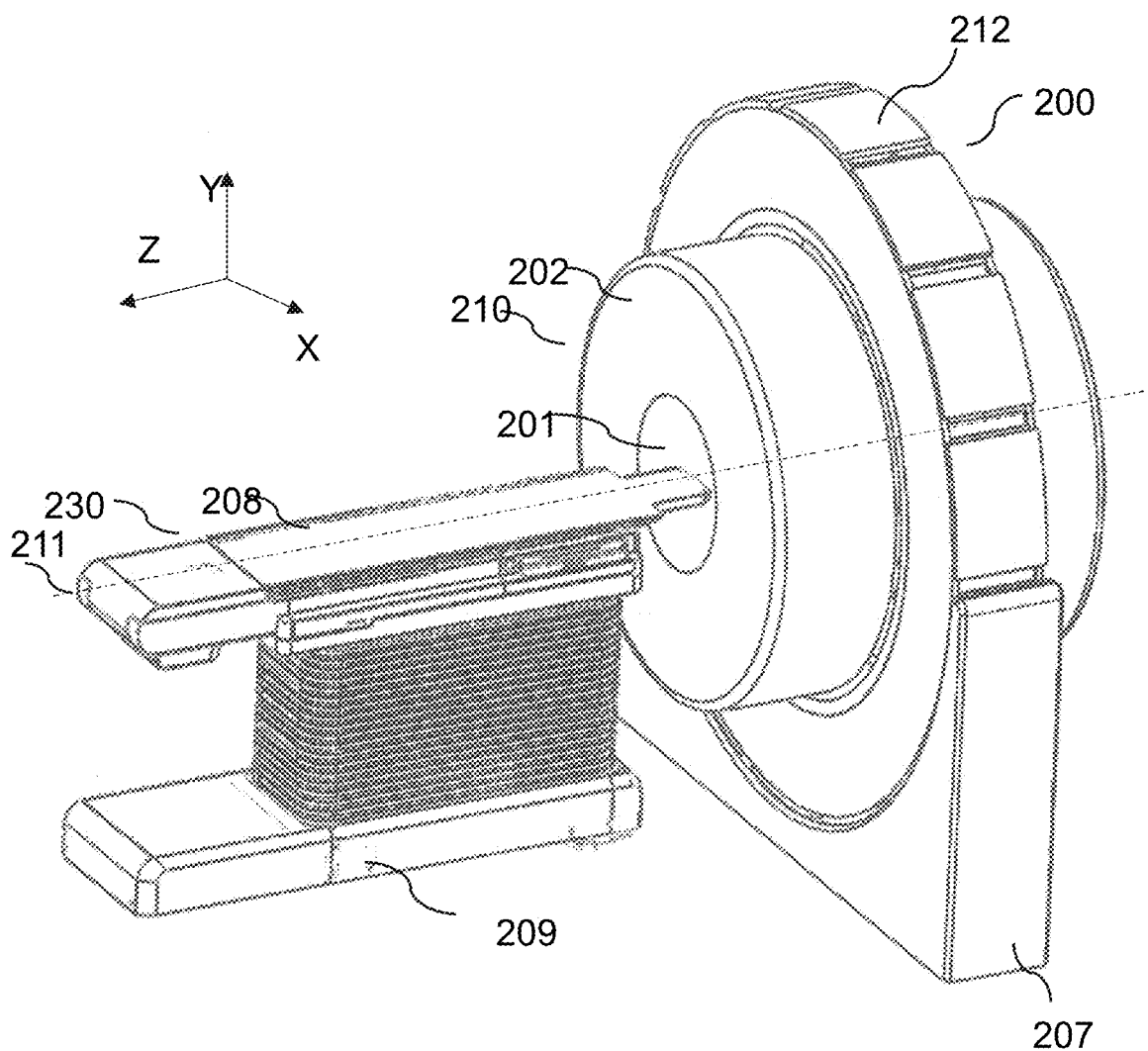
FIG. 2A illustrates an exemplary therapeutic apparatus according to some embodiments of the present disclosure.

FIG. 2A illustrates an exemplary therapeutic apparatus according to some embodiments of the present disclosure. As illustrated in FIG. 3A, therapeutic apparatus 110 may include an imaging device 210, a radiation therapy device 200, and a treatment table 230. Merely for illustration, the imaging device 210 may be an MRI scanner. In some embodiments, the MRI scanner 210 may generate MRI data, and the radiation therapy device 200 may apply the therapeutic radiation to at least one portion of a subject immobilized by the preheated immobilizing component when the immobilizing device is preheated to a certain temperature. In some embodiments, the certain temperature may be a recommended heating temperature output by a predictive model. In some embodiments, the certain temperature may be a specified temperature set by a user (e.g., a doctor, a patient, etc.). In some embodiments, the specified temperature may be equal to the recommended heating temperature. In some embodiments, the specified temperature may be different from the recommended heating temperature, for example, lower than the recommended heating temperature. In such case, the radiation therapy device 200 may be configured to prepare a preliminary workflow (e.g., parameters setting for radiation therapy) before the immobilizing component is preheated to the recommended heating temperature. The time of the entire radiation therapy may be shortened to some extent.

The MRI scanner 210 may include a bore 201, a magnetic body 202, one or more gradient coils (not shown), and one or more radiofrequency (RF) coils (not shown). The MRI scanner 210 may be configured to acquire image data from an imaging region. For example, the image data may relate to the treatment region associated with a lesion (e.g., a tumor). In some embodiments, the MRI scanner 210 may be a permanent magnet MRI scanner, a superconducting electromagnet MRI scanner, or a resistive electromagnet MRI scanner, etc., according to the types of the magnetic body 202. In some embodiments, the MRI scanner 210 may be a high-field MRI scanner, a mid-field MRI scanner, and a low-field MRI scanner, etc., according to the intensity of the magnetic field. In some embodiments, the MRI scanner 210 may be of a closed-bore (cylindrical) type, an open-bore type, or the like.

The magnetic body 202 may have the shape of an annulus and may generate a static magnetic field B0. The magnetic body 202 may be of various types including, for example, a permanent magnet, a superconducting electromagnet, a resistive electromagnet, etc. The superconducting electromagnet may include niobium, vanadium, technetium alloy, etc.

The one or more gradient coils may generate magnetic field gradients to the main magnetic field B0 in the X, Y, and/or Z directions (or axes). In some embodiments, the one or more gradient coils may include an X-direction (or axis) coil, a Y-direction (or axis) coil, a Z-direction (or axis) coil, etc. For example, the Z-direction coil may be designed based on a circular (Maxwell) coil, the X-direction coil and the Y-direction coil may be designed on the basis of the saddle (Golay) coil configuration. As used herein, the X direction may also be referred to as the readout (RO) direction (or a frequency encoding direction), the Y direction may also be referred to as the phase encoding (PE) direction, the Z direction may also be referred to as the slice-selection encoding direction. In the present disclosure, the readout direction and the frequency encoding direction may be used interchangeably.

Merely by way of example, the gradient magnetic fields may include a slice-selection gradient field corresponding to the Z-direction, a phase encoding (PE) gradient field corresponding to the Y-direction, a readout (RO) gradient field corresponding to the X-direction, etc. The gradient magnetic fields in different directions may be used to encode the spatial information of MR signals. In some embodiments, the gradient magnetic fields may also be used to perform at least one function of flow encoding, flow compensation, flow dephasing, or the like, or any combination thereof.

The one or more RF coils may emit RF pulses to and/or receive MR signals from a subject (e.g., a body, a substance, an object) being examined. As used herein, an RF pulse may include an excitation RF pulse and a refocusing RF pulse. In some embodiments, the excitation RF pulse (e.g., a 90-degree RF pulse) may tip magnetization vector away from the direction of the main magnetic field BO. In some embodiments, the refocusing pulse (e.g., a 180-degree RF pulse) may rotate dispersing spin isochromatic about an axis in the transverse plane so that magnetization vector may rephase at a later time. In some embodiments, the RF coil may include an RF transmitting coil and an RF receiving coil. The RF transmitting coil may emit RF pulse signals that may excite the nucleus in the subject to resonate at the Larmor frequency. The RF receiving coil may receive MR signals emitted from the subject. In some embodiments, the RF transmitting coil and RF receiving coil may be integrated into one single coil, for example, a transmitting/receiving coil. The RF coil may be one of various types including, for example, a quotient difference (QD) orthogonal coil, a phase-array coil, etc. In some embodiments, different RF coils 240 may be used for the scanning of different parts of a body being examined, for example, a head coil, a knee joint coil, a cervical vertebra coil, a thoracic vertebra coil, a temporomandibular joint (TMJ) coil, etc. In some embodiments, according to its function and/or size, the RF coil may be classified as a volume coil and a local coil. For example, the volume coil may include a birdcage coil, a transverse electromagnetic coil, a surface coil, etc. As another example, the local coil may include a solenoid coil, a saddle coil, a flexible coil, etc.

The radiation therapy device 200 may include a drum 212 and a pedestal 207. The drum 212 may have the shape of an annulus. The drum 212 may be disposed around the magnetic body 202 and intersect the magnetic body 202 at a central region of the magnetic body 202 along the axis 211 of the bore 201. The drum 212 may accommodate and support a radiation source that is configured to emit a radiation beam towards the treatment region in the bore 201. The radiation beam may be an X-ray beam, an electron beam, a gamma ray source, a proton ray source, etc. The drum 212, together with the radiation source mounted thereon, may be able to rotate around the axis 211 of the bore 201 and/or a point called the isocenter. Merely by way of example, the drum 212, together with the radiation source mounted thereon, may be able to rotate any angle, e.g., 90 degrees, 180 degrees, 360 degrees, 450 degrees, 540 degrees, around the axis 211. The drum 212 may be further supported by the pedestal 207.

It should be noted that the above description is merely provided for the purposes of illustration, and not intended to limit the scope of the present disclosure. For persons having ordinary skills in the art, multiple variations or modification may be made under the teaching of the present disclosure. For example, the radiation therapy device 200 may further include a linear accelerator configured to accelerate electrons, ions, or protons, a dose detecting device, a temperature controlling device (e.g., a cooling device), a multiple layer collimator, or the like, or any combination thereof. However, those variations and modifications do not depart from the scope of the present disclosure.

The treatment table 230 may include a supporting platform 208 and a base frame 209. In some embodiments, the supporting platform 208 may move along the horizontal direction and enter into the bore 201 of the MRI scanner 210. In some embodiments, the supporting platform 208 may move two-dimensionally, or three-dimensionally. In some embodiments, the supporting platform 208 may move to compensate the variance (e.g., position change) of the tumor estimated by, for example, a real-time MRI image obtained during a treatment.

In some embodiments, the subject may be placed on the supporting platform 208 and sent into the MRI device. In some embodiments, the subject may be a human patient. The human patient may lie on the back, lie in prone, lie on the side on the supporting platform 208. In some embodiments, the subject may be positioned or immobilized by an immobilizing device connected to the supporting platform 208 (e.g., via a mechanical connection). For example, the immobilizing device may be secured on the supporting platform 208, and the subject may be placed on the immobilizing device. The immobilizing device may be configured to immobilize at least a portion of the subject. The immobilizing device may include, for example, a vacuum cushion. In some embodiments, the immobilizing device may be a heatable immobilizing device (e.g., an immobilizing device 500 shown in FIG. 5A). The immobilizing device may be preheated to a preferable temperature for the subject by the preheating system 160 or the therapeutic apparatus 110 directly. For example, the preferable temperature may be configured directly by a temperature controller 530 shown in FIG. 5A. As another example, the preferable temperature may be determined according to a predictive model (e.g., a trained CNN model). During the radiation therapy treatment, although the treatment environment is at a relatively low temperature, the subject would feel warm and comfortable due to the preheated immobilizing device.

During the radiation therapy treatment, the drum 212 may be set to rotate around the magnetic body 202. In some embodiments, the magnetic body 202 may include a recess (not shown) at its outer wall. The recess may be disposed around the entire circumference of the magnetic body 202. For example, the recess may have the shape of an annulus surrounding the magnetic body 202, thus accommodating at least part of the drum 212. In some embodiments, the recess may be disposed around part of the circumference of the magnetic body 202. For example, the recess may have the shape of one or more arcs around the magnetic body 202.

In some embodiments, the radiation source may move along an entire path of rotation within the recess. The radiation source may generate the radiation beam according to one or more parameters. Exemplary parameter may include a parameter of the radiation beam, a parameter of the radiation source, or a parameter of the supporting platform 208. For example, the parameter of the radiation beam may include an irradiating intensity, an irradiating angle, an irradiating distance, an irradiating area, an irradiating time, an intensity distribution, or the like, or any combination thereof. The parameter of the radiation source may include a position, a rotating angle, a rotating speed, a rotating direction, the configuration of the radiation source, or the like, or any combination thereof. In some embodiments, the generation of the radiation beam by the radiation source may take into consideration energy loss of the radiation beam due to, e.g., the magnetic body 202 located in the pathway of the radiation beam that may absorb at least a portion of the radiation beam. For example, the irradiating intensity of the radiation beam may be set larger than that in the situation in which there is no energy loss due to, e.g., the absorption by the magnetic body 202 accordingly to compensate the energy loss such that the radiation beam of a specific intensity may impinge on a treatment region (e.g., a tumor).

Figure 2B:
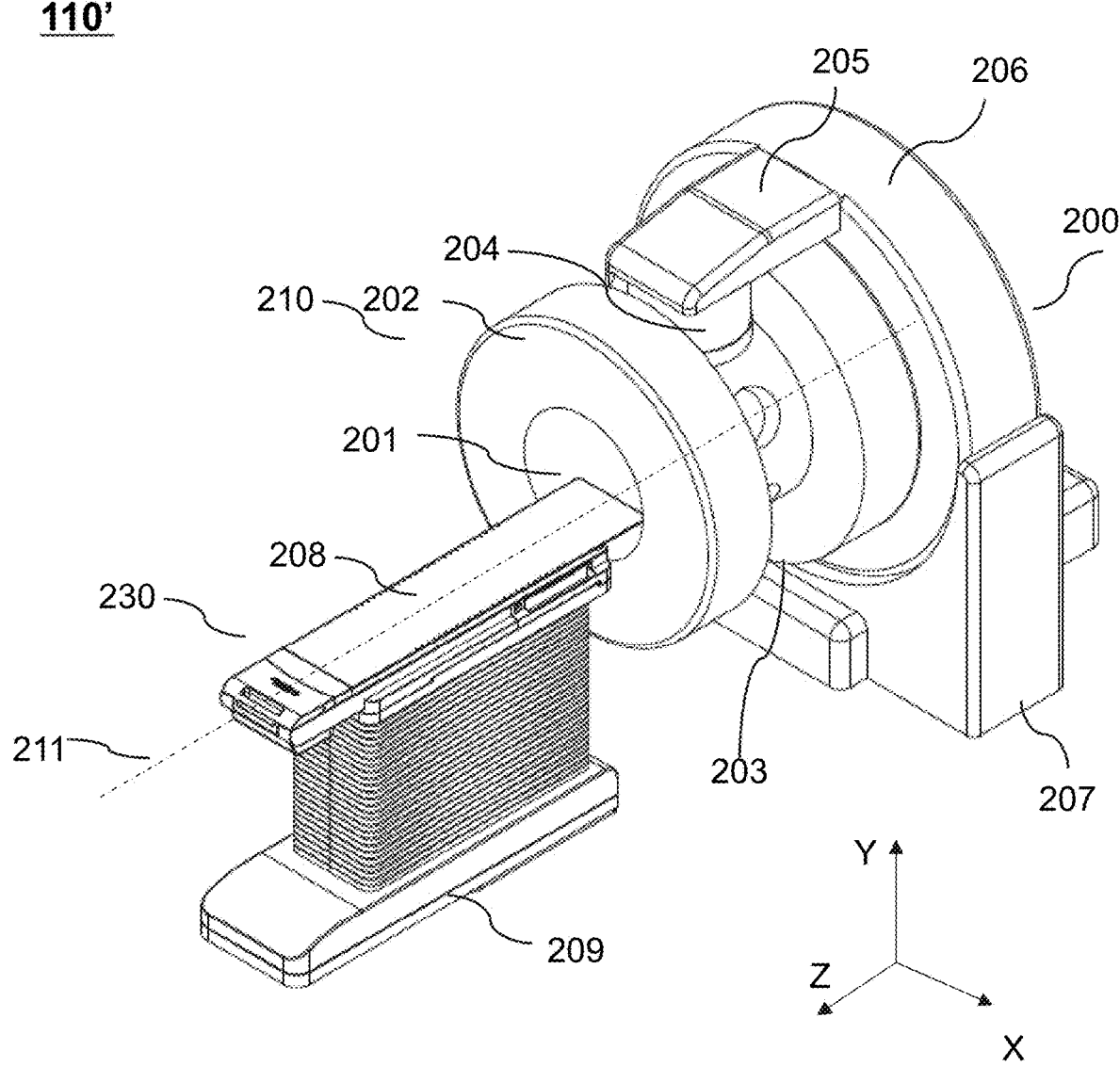
FIG. 2B illustrates another exemplary therapeutic apparatus according to some embodiments of the present disclosure.

FIG. 2B illustrates another exemplary therapeutic apparatus 110' according to some embodiments of the present disclosure. Compared with the therapeutic apparatus 110 described in FIG. 2A, the therapeutic apparatus 110' may use a gantry 206 instead of the drum 212. The gantry 206 may be disposed at one side of the magnetic body 202. A treatment head 204 may be installed on the gantry 206 via a treatment arm 205. The treatment head 204 may accommodate the radiation source. The gantry 206 may be able to rotate the treatment head 204 around the axis 211 of the bore 201.

As shown in FIG. 2B, a recess 203 may be formed at the outer wall of the magnetic body 202 and have the shape of an annulus. The recess 203 may accommodate at least a portion of the treatment head 204 and provide a path for rotation of the treatment head 204. This arrangement may reduce the distance between the treatment head 204 and the axis 211 of the bore 201 along the radial direction of the magnetic body 202. In some embodiments, the reduction of the distance between the treatment head 204 and the axis 211 of the bore 201 may increase the radiation dose that may reach the treatment region (e.g., a tumor) which leads to an enhancement in the therapeutic efficiency. In some embodiments, the width of the recess 203 along the Z direction (i.e., the axial direction of the magnetic body 202) may be no less than the width of the treatment head 204 along the Z direction.

It should be noted that the above description of the therapeutic apparatus 110 is merely provided for the purposes of illustration, and not intended to limit the scope of the present disclosure. For persons having ordinary skills in the art, multiple variations and modifications may be made under the teachings of the present disclosure. For example, the assembly and/or function of the therapeutic apparatus 110 may vary or change according to a specific implementation scenario. In some embodiments, the magnetic body 202 of the MRI scanner 210 may also rotate relative to the treatment head 204. For example, the radiation therapy device 200 and the MRI scanner 210 may synchronously or asynchronously rotate around a same axis (e.g., the axis 211). However, those variations and modifications do not depart from the scope of the present disclosure.

Figure 3:
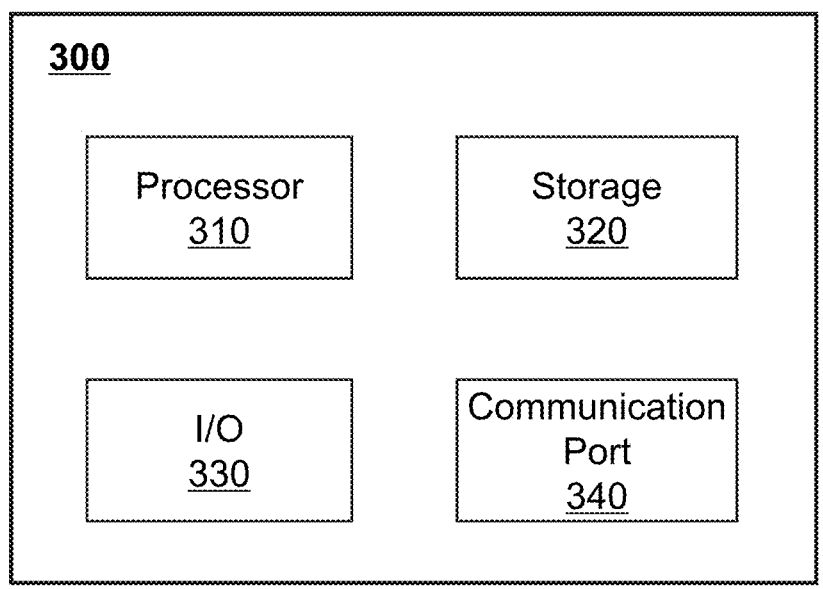
FIG. 3 is a schematic diagram illustrating hardware and/or software components of an exemplary computing device on which the processing device may be implemented according to some embodiments of the present disclosure.

FIG. 3 is a schematic diagram illustrating hardware and/or software components of an exemplary computing device on which the processing device 120 may be implemented according to some embodiments of the present disclosure. As shown in FIG. 3, a computing device 300 may include a processor 310, a storage 320, an input/output (I/O) 330, and a communication port 340.

The processor 310 may execute computer instructions (or program codes) and perform functions of the processing device 120 in accordance with techniques described herein. The computer instructions may include, for example, routines, programs, objects, components, signals, data structures, procedures, modules, and functions, which perform particular functions described herein. For example, the processor 310 may process data obtained from the therapeutic apparatus 110, the storage device 140, one or more terminal devices 150, and/or any other component of the radiation therapy system 100. Specifically, the processor 310 may process characteristics information of the subject to determine a preheating temperature of the immobilizing device. For example, the processor 310 may generate a control signal for applying the therapeutic radiation, and send the control signal to the radiation therapy apparatus. As another example, the processor 310 may perform instructions obtained from the terminal device(s) 150. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the therapeutic apparatus 110, the storage device 140, one or more terminal devices 150, the preheating system 160, and/or any other component of the radiation therapy system 100. In some embodiments, the storage 320 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for applying the therapeutic radiation.

The I/O 330 may input or output signals, data, and/or information. In some embodiments, the I/O 330 may enable user interaction with the processing device 120. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected with a network (e.g., the network 130) to facilitate data communications. The communication port 340 may establish connections between the processing device 120 and the therapeutic apparatus 110, the storage device 140, one or more terminal devices 150, or the preheating system 160. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
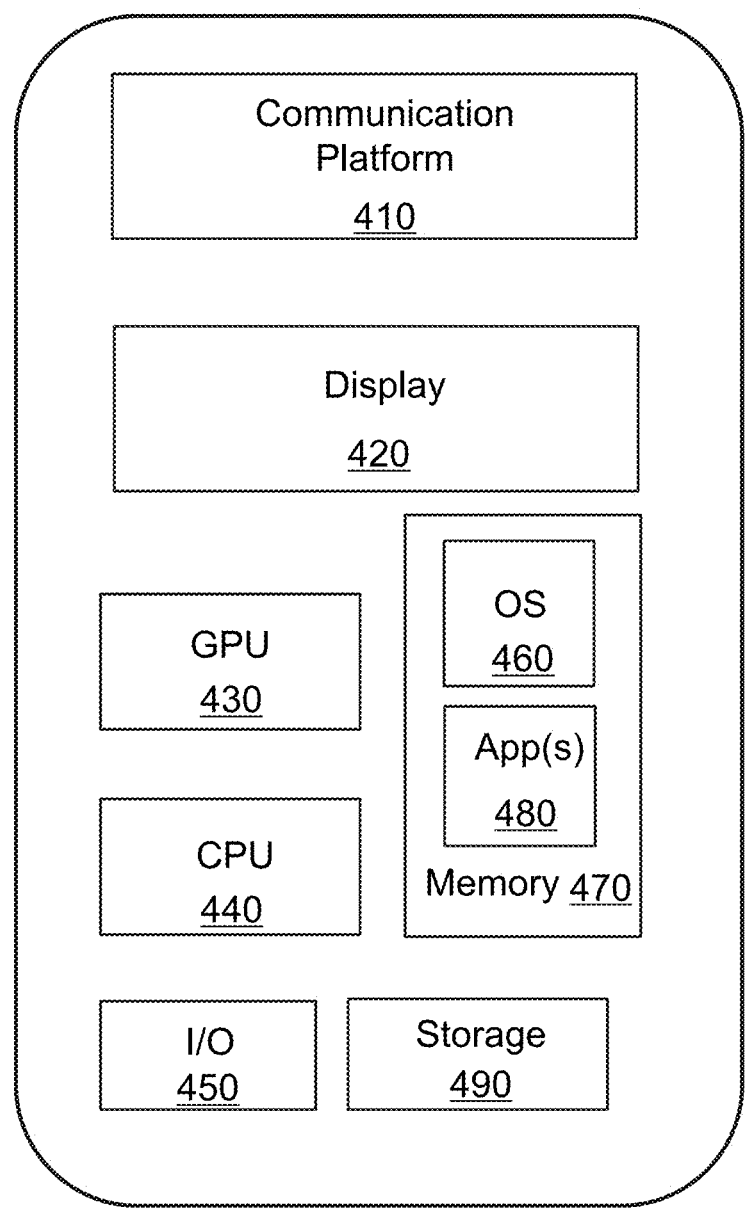
FIG. 4 is a block diagram illustrating an exemplary processing device according to some embodiments of the present disclosure.

FIG. 4 is a schematic diagram illustrating hardware and/or software components of an exemplary mobile device according to some embodiments of the present disclosure. As illustrated in FIG. 4, a mobile device 400 may include a communication platform 410, a display 420, a graphics processing unit (GPU) 430, a central processing unit (CPU) 440, an I/O 450, a memory 470, and storage 490. In some embodiments, any other suitable component, including but not limited to a system bus or a controller (not shown), may also be included in the mobile device 400. In some embodiments, a mobile operating system 460 (e.g., iOS, Android, Windows Phone, etc.) and one or more applications 480 may be loaded into the memory 470 from the storage 390 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the radiation therapy system 100 via the network 130.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 5A:
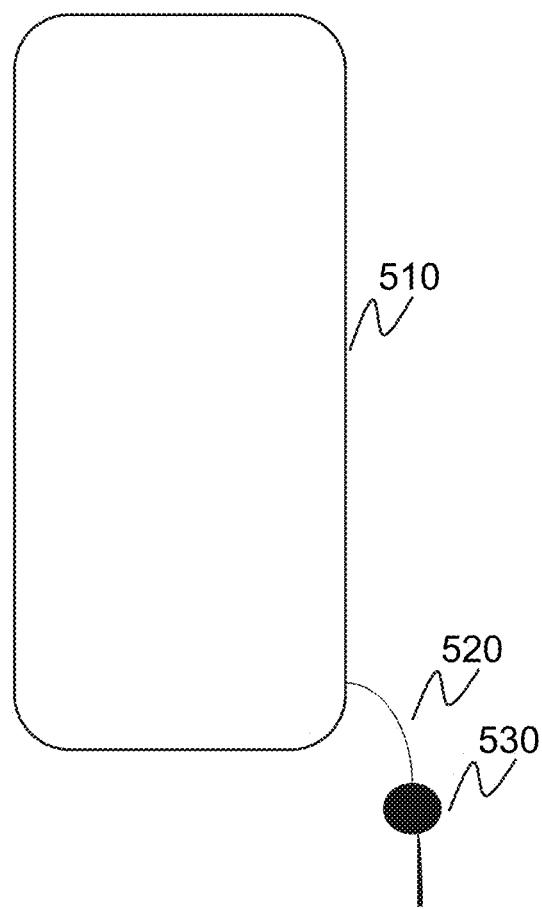
FIG. 5A is a schematic diagram illustrating an exemplary immobilizing device according to some embodiments of the present disclosure.

FIG. 5A is a schematic diagram illustrating an exemplary immobilizing device according to some embodiments of the present disclosure. In some embodiment, the immobilizing device 500 may be a heatable and moldable vacuum cushion. As shown in FIG. 5A, the immobilizing device 500 may include a body 510, a lead wire 520 and a temperature controller 530.

Figure 5B:
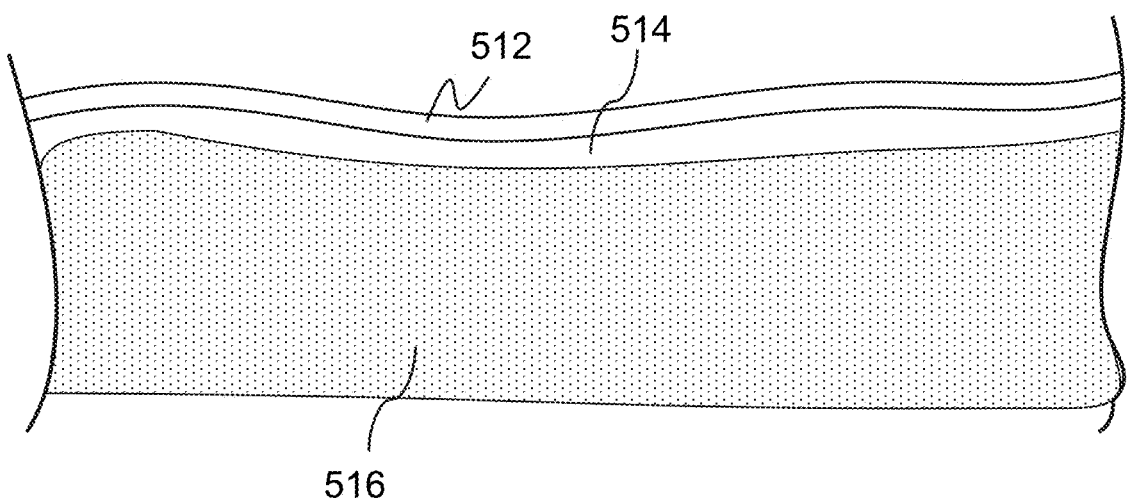
FIG. 5B is a cross-sectional view of a portion of an exemplary immobilizing device according to some embodiments of the present disclosure.

There are multiple components or material layers disposed inside the body 510. Merely for illustration, FIG. 5B illustrates a cross-sectional view of a portion of a body of an exemplary immobilizing device (e.g., the body 510 of the immobilizing device 500). As shown in FIG. 5B, the body 510 may include a shell 512, a heating element 514 and a filler material 516. In some embodiments, the shell 512 may be made from a soft and flexible material, such as an air impermeable material, a thermoplastic material, or a heat-resistant material. In some embodiments, the shell 512 may include a valve that is connectable to a vacuum source (e.g., a vacuum compressor or a vacuum pump). The valve (not shown in FIG. 5B) may be installed on a top surface of the shell 512. The valve may be used to inflate and deflate the vacuum cushion. For example, a partial vacuum may be created by evacuating air from the cushion through the valve using the vacuum pump. The cushion may be molded around the subject's body contours and the remaining air may be evacuated through the valve. The molded vacuum cushion may be secured on the top of supporting platform of the treatment table (e.g., the supporting platform 208 shown in FIG. 2A). The mold vacuum cushion may accommodate the subject. In some embodiments, when the vacuum cushion is molded for the first use, the vacuum cushion may keep the shape molded in later use, in case that the vacuum cushion needed be molded repeatedly in later use. In some embodiments, the heating element 514 may be attached to an inner side of the shell 512. The heating element 514 may heat the vacuum cushion to a configured heating temperature under a heating voltage. The configured heating temperature may be the preferable temperature for the subject. When the subject lies on the heated vacuum cushion, he/she would feel warm and comfortable although the treatment environment is at a relatively low temperature. In some embodiments, the heating element 514 may be flexible and deformed with the inflation and the deflation of the cushion. For example, the heating element 514 may be a flexible heating film. In some embodiments, the heating element 514 may not be allowed to interfere a radiation dose (e.g., a dose of X-rays) that the subject receives in case to cause a poor effect for the therapeutic radiation. In some cases, the heating element 514 may be not designed as a metallic heating element because the metallic element included in the metallic heating element interferes the radiation beam. In some embodiments, the heating element 514 may be a flexible heating film that does not interfere a radiation beam generated by the radiation source. For example, the flexible heating film may include a Carbon fiber heating film, or a Graphene heating film, etc. In some embodiments, the heating element 514 may be electrically connected to an electrical circuit. The electrical circuit may be used to supply a heating voltage to the heating element 514 for preheating the vacuum cushion. For example, the electrical circuit may be included in or connected to the lead wire 520 shown in FIG. 5A. The lead wire 520 may be operably connected to an external power source through a plug or a conductive interface. The power source may provide the heating voltage to the heating element 514 via the lead wire 520. In some embodiments, the filler material 516 may be contained within a region defined by the shell 512. For example, the filler material 516 may be filled in the region under the shell 512 and the heating element 514. The filler material 516 may include foam particles, sponge, cotton, or the like, or a combination thereof. The foam particles may include one or more polymer materials such as resin, fiber, rubber, etc. The resin may include phenolic, urea-formaldehyde, melamine-formaldehyde, epoxy, polyurethane, polyimide, polymethyl methacrylate (PMMA), acrylonitrile butadiene styrene (ABS), polyamide, polylactic acid (PLA), polybenzimidazole (PBI), polycarbonate (PC), polyethersulfone (PES), polyetheretherketone (PEEK), polyethylene (PE), polyphenylene oxide (PPO), polyphenylene sulfide (PPS), polypropylene (PP), polystyrene (PS), polyvinyl chloride (PVC), etc. The sponge may include nature cellulose, foamed resin, etc. The foamed resin may include polyether, polyester, polyvinyl alcohol, etc.

Referring back to FIG. 5A, the body 510 may also include or be operably coupled to a temperature sensor for detecting a heating temperature of the vacuum cushion in real time or near real time. In some embodiments, the temperature sensor (not shown in FIG. 5A) may be disposed in the body 510. Exemplary temperature sensor may include a thermocouple sensor, a thermistor sensor, a resistance temperature detector (RTD), an IC temperature sensor, or the like, or any combination thereof.

In some embodiments, the temperature sensor may communicate with a temperature controller (e.g., the temperature controller 530 shown in FIG. 5A). The temperature controller 530 may be configured to control or configure the heating temperature of the vacuum cushion. For example, a user may configure the preferable heating temperature for the subject through an interface of the temperature controller 530 (e.g., a display unit). When the temperature sensor detects that the temperature of the vacuum cushion arrives at the preferable heating temperature, the temperature controller 530 may stop heating the vacuum cushion. As another example, the temperature controller 530 may receive a preheating instruction from the preheating system 160 via the network 130. In response to the preheating instruction, the temperature controller 530 may be used to automatically preheat the vacuum cushion. It should be noted that the immobilizing device 500 need to be electrically connected to the power source before the preheating. The preheating instruction may include one or more preheating parameters, such as a heating temperature, a preheating start time, a preheating end time, a heating voltage, and so on. In some embodiments, the temperature controller 530 may be powered by the power source via the lead wire 520.

In some embodiments, the temperature controller 530 may have a temperature memory function for recording a previously configured preferable temperature for the subject. For example, the temperature controller 530 may include a temperature memory unit. The temperature memory unit may record the previously configured preferable temperature. The temperature controller 530 may directly configure the recorded preferable temperature as the heating temperature of the vacuum cushion. There is no need to reconfigure the heating temperature of the vacuum cushion when preheating the vacuum cushion again, which may save preheating time and improve a treatment efficiency of the radiation therapy system to some extent.

Merely for illustration, assuming that the preferable heating temperature of a subject is 25 degrees Celsius, the temperature controller 530 may be configured to set 24 degrees Celsius as the heating temperature of the vacuum cushion of the subject when first preheating the vacuum cushion. The temperature memory unit may record the first configured heating temperature, that is, 25 degrees Celsius. When preheating the vacuum cushion in later treatment process, the temperature controller 530 may directly configure 25 degrees Celsius as the heating temperature of the vacuum cushion instead of artificial configuration operation.

In some embodiments, the immobilizing device 500 may be preheated by the preheating system 160 or the therapeutic apparatus 110. The preheating system 160 may be separated from the therapeutic apparatus 110. For example, the preheating system 160 may receive a preheating request for the immobilizing device 500. In response to the preheating request, the preheating system 160 may perform one or more preheating operations for the immobilizing device 500, for example, determining a preheating time, determining a preferable temperature according to a predictive model or by setting manually, and so on. After the immobilizing device 500 may be preheated to the preferable temperature, the subject or the technician may carry the preheated immobilizing device to the treatment room where therapeutic apparatus 110 is, and mount the preheated immobilizing device on the supporting platform 208 of the treatment table 230. The subject may be secured on the preheated vacuum cushion to receive the treatment. As another example, the immobilizing device 500 may be directly preheated through the therapeutic apparatus 110. The immobilizing device 500 that is not be preheated may be mounted on the supporting platform 208 of the treatment table 230. The therapeutic apparatus 110 may be configured to configure the preheating parameters of the immobilizing device 500. Then the therapeutic apparatus 110 may begin to preheat the immobilizing device 500 according to the preheating parameters. After completing the preheating, the subject may lie on the preheated vacuum cushion to receive the treatment. In some embodiments, the preheating system 160 or the therapeutic apparatus 110 may be configured to preheat the vacuum cushion according to a predictive model. The predictive model may be used to output a recommended preheating temperature for the subject. The vacuum cushion may be preheated to the recommended temperature. More descriptions of the predictive model may be found elsewhere in the present disclosure (e.g., FIGS. 8-9, and the description thereof).

Figure 6:
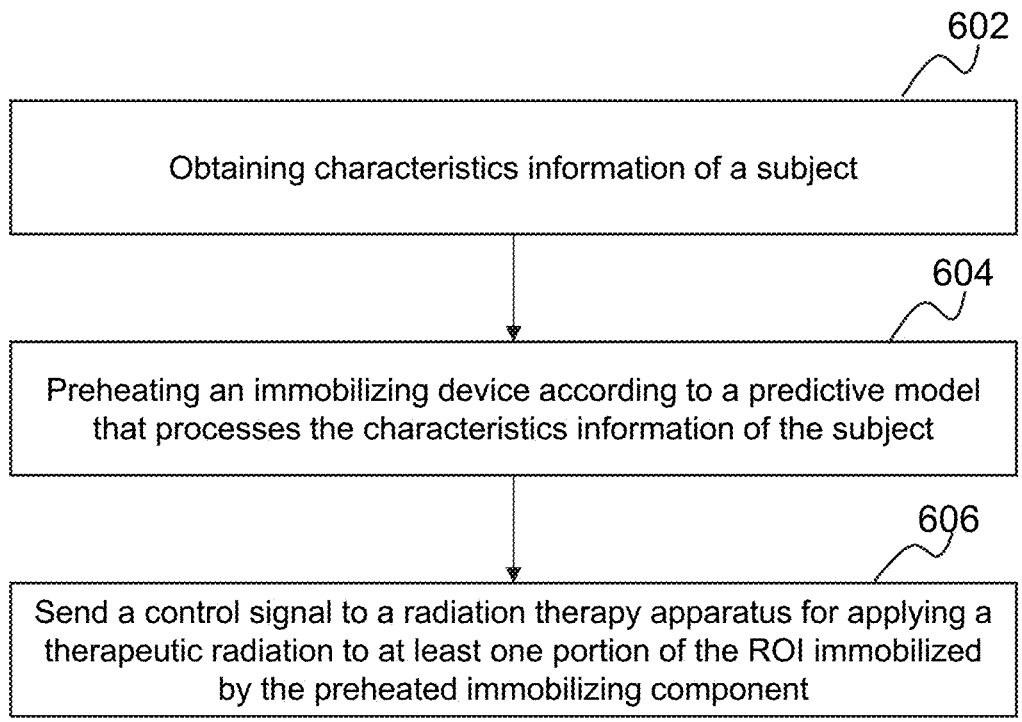
FIG. 6 is a flowchart illustrating an exemplary process for applying a therapeutic radiation in a radiation therapy system according to some embodiments of the present disclosure.

FIG. 6 is a flowchart illustrating an exemplary process for applying a therapeutic radiation in a radiation therapy system according to some embodiments of the present disclosure. In some embodiments, one or more operations of process 600 illustrated in FIG. 6 may be implemented in the radiation therapy system 100 illustrated in FIG. 1. For example, the process 600 illustrated in FIG. 6 may be stored in the storage device 140 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 602, characteristics information of a subject may be obtained. For example, the processing device 120 may obtain the characteristics information of the subject from a storage device (e.g., the storage device 140). In some embodiments, the subject may be a human patient. In some embodiments, the characteristics information of the subject may include a height, a weight, an age, a gender, a lesion, radiation parameters (e.g., a dose of X rays, a field width, a pitch, a modulation factor, etc.), or the like, or a combination thereof. In some embodiments, the characteristics information may be included in a radiation therapy planning protocol regarding the subject. Before performing the therapeutic radiation, the radiation therapy planning protocol may be input to the radiation therapy system 100 via an I/O component (e.g., the I/O 330 shown in FIG. 3). The radiation therapy planning protocol may be stored in the storage device 140. The processing device 120 may parse the radiation therapy planning protocol to obtain the characteristics information of the subject. In some embodiments, the characteristics information of the subject may be included in a preheating request sent by the terminal device 150. The processing device 120 may parse the preheating request to obtain the characteristics information of the subject.

In 604, an immobilizing device (e.g., the immobilizing device 500 shown in FIG. 5A) may be preheated according to a predictive model that processes the characteristics information of the subject. In some embodiments, one or more preheating operations may be performed by a preheating system (e.g., the preheating system 160) or a therapeutic apparatus (e.g., the therapeutic apparatus 110 of the radiation therapy system 100).

Before the radiation therapy treatment, the immobilizing device may be preheated to a preferable temperature for the subject so that the subject may feel comfortable in the relatively low-temperature treatment room when the subject is secured on the preheated immobilizing device. Specifically, the processing device 120 may obtain the predictive model from the storage device 140. The predictive model may be used to output a recommended heating temperature by processing the characteristics information of the subject. The processing device 120 may determine the recommended heating temperature for the subject based on the predictive model. In some embodiments, the preheating system 160 may obtain the recommended heating temperature from the processing device 120 via the network 130. The preheating system 160 may preheat the immobilizing device to the recommended heating temperature. After completing the preheating operation, the preheated immobilizing device may be mounted on the supporting platform of the treatment table of the therapeutic apparatus 110. At least one portion of the ROI of the subject may be positioned or immobilized by the preheated immobilizing device. A corresponding therapeutic radiation may be applied to the at least one portion of the subject. In some embodiments, the therapeutic apparatus 110 may directly preheat the immobilizing device. For example, the immobilizing device may be mounted on the supporting platform of the treatment table of the therapeutic apparatus 110 before the preheating. The therapeutic apparatus 110 may obtain the recommended heating temperature from the processing device 120 via the network. The therapeutic apparatus 110 may preheat the immobilizing device to the recommended heating temperature. After the completing the preheating operation, the subject may lie on the preheated immobilizing device to wait for a corresponding therapeutic radiation. At least one portion of the ROI of the subject may be positioned or immobilized by the preheated immobilizing device. In some embodiments, the therapeutic apparatus 110 may preheat the immobilizing device to a specified temperature. The specified temperature may be equal to or different from the recommended heating temperature. For example, assume that the specified temperature is lower than the recommended heating temperature, when the immobilizing device is preheated to the specific temperature, the therapeutic apparatus 110 (e.g., the radiation therapy device 200 in the therapeutic apparatus 110) may be configured to prepare a preliminary workflow (e.g., parameters setting for radiation therapy) before the immobilizing component is preheated to the recommended heating temperature. The time of the entire radiation therapy may be shortened to some extent.

In some embodiments, the predictive model may be generated by training an initial model using a machine learning algorithm. For example, the processing device 120 may obtain a set of training data (also referred to herein as a training set) from a database (e.g., the storage device 140). The database may record information regarding a plurality of subjects receiving the therapeutic radiation, such as characteristics information of the plurality of subjects, preheating data of the immobilizing devices corresponding to the plurality of subjects. The obtained training set may include labeled historical preheating data of the immobilizing components corresponding to the plurality of subjects and the characteristics of the plurality of subjects. The processing device 120 may train the initial model based on the training data. During the training, the processing device 120 may iteratively update parameters of the initial model by minimizing a loss function of the initial model. If the loss function is convergent or a training loss value of the loss function is less than or equal to a threshold, the processing device 120 may determine the predictive model, and terminate the training process. The trained predictive model may be used to determine a recommended heating temperature by processing the characteristics information of a current subject. In some embodiments, the trained predictive model may be stored in the storage device 140. More descriptions of the generation of the predictive model may be found elsewhere in the present disclosure (e.g., FIG. 8-9, and the descriptions thereof).

In 606, a control signal may be sent to the therapeutic apparatus (e.g., the therapeutic apparatus 110) for applying the therapeutic radiation to the at least one portion of the ROI immobilized by the preheated immobilizing component.

As described above, the preheated immobilizing device (e.g., a preheated vacuum cushion) may be mounted on the supporting platform of the treatment table of the therapeutic apparatus. The subject may be placed on the preheated immobilizing device, and at least one portion of the ROI of the subject may be immobilized by the preheated immobilizing device. The therapeutic apparatus (e.g., the radiation therapy device 200 in the therapeutic apparatus 110) may receive a control signal to apply the therapeutic radiation. In some embodiments, the control signal may be generated by the processing device 120. For example, the processing device 120 may generate the control signal in response to the immobilizing device being preheated to the preferable temperature. As another example, the control signal may be determined based on an image regarding the at least one portion of the ROI. More descriptions regarding the determining the control signal based on the image of the at least one portion of the ROI may be found elsewhere in the present disclosure. See, FIG. 7 and the descriptions thereof. In some embodiments, the control signal may be inputted by a user (e.g., a doctor) through the terminal device 150. For example, the user may press a button for controlling the therapeutic apparatus to apply the therapeutic radiation to the at least one portion of the ROI. In some embodiments, the control signal may include parameters associated with the therapeutic radiation on a lesion (e.g., a tumor). For example, the control signal may include the dosage of X-rays and a duration of the radiation beam. As another example, the control signal may include parameters of the multi-leaf collimator (MLC) that determines the shape of the radiation beam projected on the subject. The MLC may include a plurality of individual leaves of high atomic numbered materials (e.g., tungsten) moving in and out of the path of the radiation beam. The movement of some or all of the plurality of leaves may be independent from each other. In some embodiments, the control signal may include parameters associated with movements of one or more components of a radiation therapy apparatus. For example, the control signal may include a parameter associated with one or more positions of a radiation source of the radiation therapy apparatus (e.g., the radiation therapy apparatus in the therapeutic apparatus 110). As another example, the control signal may include a parameter associated with a height or a position of a platform of the radiation therapy apparatus (e.g., a location of the supporting platform 208 of the treatment table 230 along an axis of the magnetic body 202) to properly position a patient so that the treatment region (e.g., a cancerous tumor) in the patient may properly receive the radiation beam from the radiation therapy apparatus.

Upon receipt of the control signal, the therapeutic apparatus (e.g., the radiation therapy device 200 in the therapeutic apparatus 110) may apply the therapeutic radiation to the at least one portion of the ROI. During a therapeutic radiation session, one or more components of the radiation therapy device may coordinate to deliver the therapeutic radiation. For instance, the radiation source of the radiation therapy device 200 may rotate; alternatively or additionally, the radiation therapy session may proceed according to a collection of parameters including, e.g., the dosage of X-rays, the duration of a radiation beam from a radiation source, the shape of the MLC, and the position of the platform, etc., that change over time cooperatively. In some embodiments, the radiation beam may be emitted only when the radiation source of the radiation therapy device rotates to certain angles (e.g., 60 degrees, 120 degrees, 180 degrees, 240 degrees, 300 degrees, 360 degrees). For example, an intensity modulated radiation therapy (IMRT) may be applied. The radiation source may stop rotating intermittently. The radiation source may rotate to a desired position, pause there, emit a radiation beam for a specific duration, and then resume to rotate. In some embodiments, the radiation source may rotate continuously, and emit a radiation beam continuously or intermittently. In some embodiments, the radiation source may continuously emit the radiation beam while rotating.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 602 and 604 may be integrated to a single operation.

Figure 7:
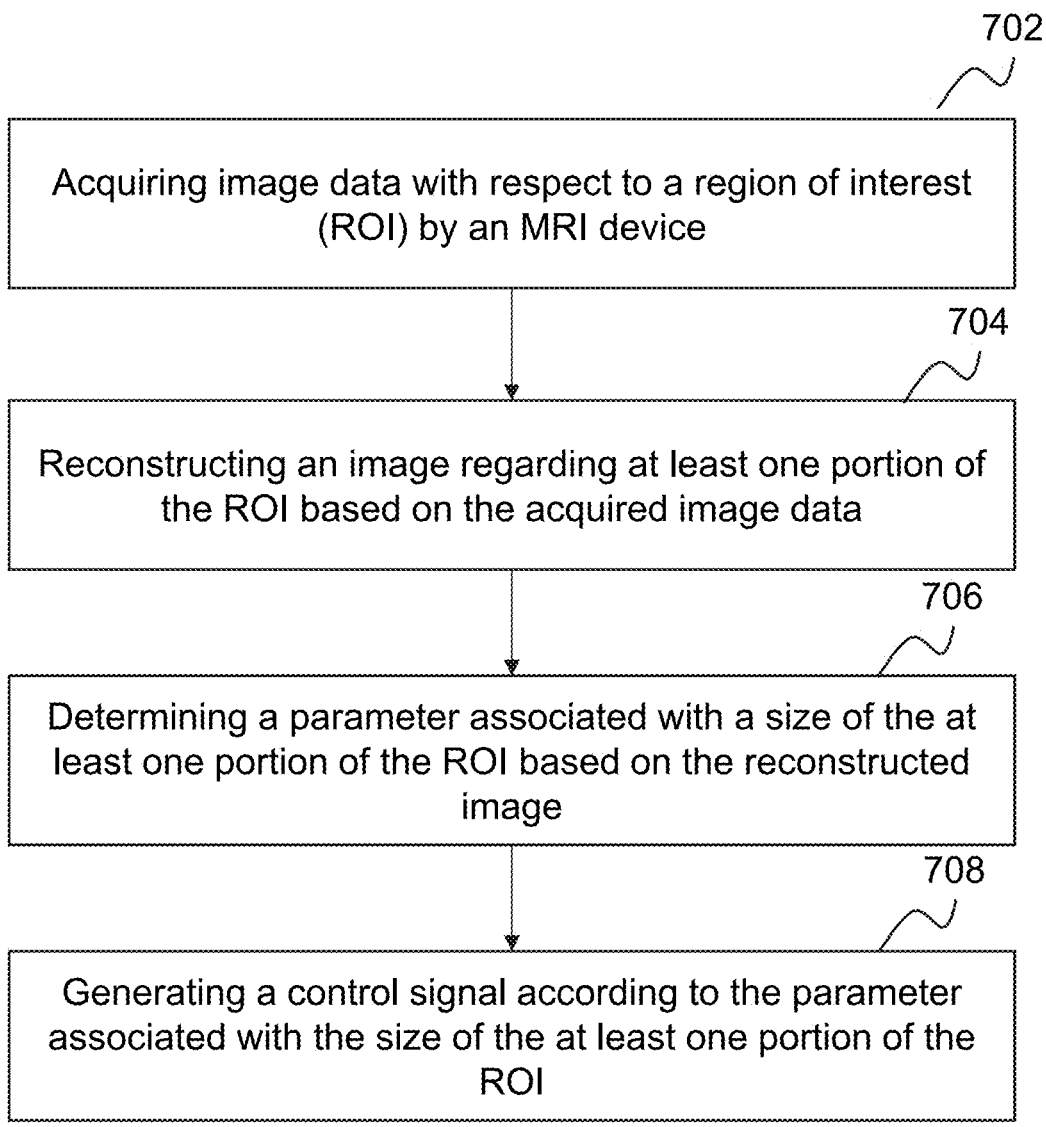
FIG. 7 is a flowchart illustrating an exemplary process for generating a control signal for applying an therapeutic radiation in a radiation therapy system according to some embodiments of the present disclosure.

FIG. 7 is a flowchart illustrating an exemplary process for generating a control signal for applying a therapeutic radiation in a radiation therapy system according to some embodiments of the present disclosure. In some embodiments, one or more operations of process 700 illustrated in FIG. 7 may be implemented in the radiation therapy system 100 illustrated in FIG. 1. For example, the process 700 illustrated in FIG. 7 may be stored in the storage device 140 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 702, the processing device (e.g., the processing device 120) may acquire image data (e.g., MRI data) with respect to a region of interest (ROI) by an imaging device (e.g., the MRI scanner 210). For example, the MRI data may be MR signals received by an RF coil from a subject. In some embodiments, an ROI may refer to a treatment region associated with a lesion (e.g., a tumor). The treatment region may be a region of a subject (e.g., a body, a substance, an object). In some embodiments, the ROI may be a specific portion of a body, a specific organ, or a specific tissue, such as head, brain, neck, body, shoulder, arm, thorax, cardiac, stomach, blood vessel, soft tissue, knee, feet, or the like, or any combination thereof.

In 704, the processing device (e.g., the processing device 120) may reconstruct an image (e.g., an MRI image) regarding the at least one portion of the ROI based on the acquired image data (e.g., the MRI data). For example, the MRI image may be reconstructed illustrating a distribution of atomic nuclei inside the subject based on the MRI data. Different kinds of imaging reconstruction techniques for the image reconstruction procedure may be employed. Exemplary image reconstruction techniques may include Fourier reconstruction, constrained image reconstruction, regularized image reconstruction in parallel MRI, or the like, or a variation thereof, or any combination thereof.

The reconstructed image (e.g., the MRI image) may be used to determine therapeutic radiation to a lesion (e.g., a tumor). For example, the processing device 120 may determine the position of the tumor and the dose of radiation according to the MRI image. In some embodiments, it may take at least several minutes to reconstruct an MRI image representing a large imaging region. In some embodiments, in order to generate the MRI image during a relatively short time period (e.g., every second), the processing device 120 may reconstruct an initial image representing a smaller imaging region (e.g., at least one portion of the ROI) as opposed to the MRI image representing a large imaging region, and then combine the initial image with the MRI image representing a large imaging region. For example, the processing device 120 may replace a portion of the MRI image representing a large imaging region related to the ROI with the initial image. The MRI image representing a large imaging region may include information of non-ROI (e.g., a healthy tissue) near the ROI and that of the ROI. In some embodiments, the MRI image representing a large imaging region may be acquired and reconstructed before a session of the radiotherapy starts. For example, the MRI image representing a large imaging region may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before the radiation source starts emitting a radiation beam for treatment. In some embodiments, the MRI image representing a large imaging region may be obtained from a storage device in the radiation therapy system 100, such as the storage device 140.

In 706, the processing device (e.g., the processing device 120) may determine a parameter associated with a size of the at least one portion of the ROI based on the reconstructed image (e.g., the MRI image). In some embodiments, the parameter associated with a size of the at least one portion of the ROI may include the size of a characteristic cross section of a lesion (e.g., a tumor) and is perpendicular to the direction of the radiation beams impinging on the at least one portion of the ROI. As used herein, a characteristic cross section of a lesion may be a cross section of the lesion, among cross sections of the lesion that are parallel to each other, whose area is the largest. In some embodiments, the ROI or a portion thereof may substantially conform to the characteristic cross section of the lesion. For instance, for an ROI having the shape of a circle, the diameter of the ROI may be the same as or slightly (e.g., no more than 5%, or 10%, or 15%, or 20%, or 25%, or 30%, or 40%, or 50%) larger than the largest dimension of the characteristic cross section of the lesion. As another example, for an ROI having the shape of an ellipse or a polygon (e.g., a square, a rectangle, etc.), the area of the ROI may be the same as or slightly (e.g., no more than 5%, or 10%, or 15%, or 20%, or 25%, or 30%, or 40%, or 50%) larger than the area of the characteristic cross section of the lesion.

In some embodiments, the parameter associated with a size of the at least one portion of the ROI may indicate the shape of the characteristic cross section of the tumor. For example, the parameter associated with a size of at least one portion of the ROI may indicate that the shape of the cross section of the tumor is a circle or an approximate circle, and further indicate the diameter of the circle or the approximate circle. In some embodiments, to determine the parameter associated with a size of at least one portion of the ROI, the processing device 120 may extract texture information from the MRI image, and determine texture features that are indicative of the ROI by identifying frequent texture patterns of the ROI in the extracted texture information. Then, the processing device 120 may measure the size of the region which includes the texture features in the MRI image, and determine the parameter associated with the size of the ROI.

In 708, the processing device (e.g., the processing device 120) may generate a control signal according to the parameter associated with the size of at least one portion of the ROI. In some embodiments, the control signal may be dynamically adjusted based on the plurality of MRI images taken at different time points. As described in connection with operation 606, the control signal may include parameters associated with the therapeutic radiation on the tumor. For example, the control signal may include the dosage of X-rays and a duration of the radiation beam. As another example, the control signal may include parameters of the multi-leaf collimator (MLC) that determines the shape of the radiation beam projected on the subject. The MLC may include a plurality of individual leaves of high atomic numbered materials (e.g., tungsten) moving in and out of the path of the radiation beam. The movement of some or all of the plurality of leaves may be independent from each other. In some embodiments, the control signal may include parameters associated with movements of one or more components of a radiation therapy apparatus. For example, the control signal may include a parameter associated with one or more positions of a radiation source of the radiation therapy apparatus (e.g., the radiation therapy device 200 in the therapeutic apparatus 110). As another example, the control signal may include a parameter associated with a height or a position of a platform of the radiation therapy apparatus (e.g., a location of the supporting platform 208 of the treatment table 230 along an axis of the magnetic body 202) to properly position a patient so that the treatment region (e.g., a cancerous tumor) in the patient may properly receive the radiation beam from the radiation therapy apparatus. In some embodiments, the generated control signal may be sent to the therapeutic apparatus for applying the therapeutic radiation to the at least one portion of the ROI.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 702 and 704 may be integrated to a single operation.

FIG. 8 is a flowchart illustrating an exemplary process for generating a predictive model according to some embodiments of the present disclosure. In some embodiments, one or more operations of process 800 illustrated in FIG. 8 may be implemented in the radiation therapy system 100 illustrated in FIG. 1. For example, the process 800 illustrated in FIG. 8 may be stored in the storage device 140 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 802, the processing device (e.g., the processing device 120) may obtain, from a database, a set of training data including labeled historical preheating data of the immobilizing components corresponding to a plurality of subjects and the characteristics of the plurality of subjects.

In some embodiments, the set of training data (also referred as the training set) may be associated with a plurality of samples. As used herein, a sample may be also referred to as a subject receiving therapeutic therapy in a historical period (e.g., a month, a quarter, a year, two years, etc.). In some embodiments, immobilizing devices corresponding to the plurality of samples may be preheated. Each of the plurality of sample may have his/her own immobilizing device for immobilizing at least one portion of ROI. The preheating data of the immobilizing devices corresponding to the plurality of samples may be stored in the database (e.g., the storage device 140). The preheating data may include a heating temperature, a preheating start time, a preheating end time, a heating voltage, or the like, or any combination thereof. In some embodiments, the characteristics information of the plurality of samples may be stored in the database (e.g., the storage device 140). The characteristics information may include a height, a weight, an age, a gender, a lesion, radiation parameters (e.g., a dosage of X rays, a field width, a pitch, a modulation factor, etc.), or the like, or any combination thereof. In some embodiments, the preheating data and the characteristics information regarding the plurality of samples may be labeled. The labeled preheating data and labeled characteristics information may be designated as the training set.

In 804, the processing device (e.g., the processing device 120) may obtain an initial model. The initial model may be a machine learning model. In some embodiments, the machine learning model may be stored in a storage device as an application or a part thereof. The machine learning model may be constructed based on at least one of a convolutional machine learning model (CNN), a fully convolutional neural network (FCN) model, a generative adversarial network (GAN), a back propagation (BP) machine learning model, a radial basis function (RBF) machine learning model, a deep belief nets (DBN) machine learning model, a long short-term memory (LSTM) model, an Elman machine learning model, or the like, or any combination thereof. In some embodiments, the machine learning model may include multiple layers, for example, an input layer, multiple hidden layers, and an output layer. The multiple hidden layers may include one or more convolutional layers, one or more pooling layers, one or more batch normalization layers, one or more activation layers, one or more fully connected layers, a cost function layer, etc. Each of the multiple layers may include a plurality of nodes. The machine learning model may be trained to take characteristics of the subject as an input and a heating temperature as an output. The output temperature may be designated as a recommended heating temperature of the immobilizing device.

In 806, the processing device (e.g., the processing device 120) may train the initial model based on the training data.

The training data may be taken as input of the initial model. During the training, the processing device 120 may iteratively update parameters by minimizing a loss function of the initial model (as illustrated in 808). The loss function may measure how far away an output solution is from an optimal solution. In some embodiments, the loss function may include a square loss function, a logistic loss function, or the like, or any combination thereof. In some embodiments, the loss function may also include a regularization term, for example, L1 norm, or L2 norm. For example, the loss function may be a combination of a square loss function and the regularization term. As another example, the loss function may be a combination of logistic loss function and the regularization term. The processing device 120 may optimize a training loss of the loss function to generate a predictive model. In each training round (or each iteration process), the processing device 120 may update the parameters of the model by using a stochastic gradient descent (SGD) algorithm.

In 810, the processing device (e.g., the processing device 120) may determine the predictive model. In some embodiments, when the training loss of the loss function is less than or equal to a threshold, the processing device 120 may terminate the training, and determine the current model as the optimal predictive model. In other words, the parameters of the current model may be designated as the parameters of the optimal predictive model. In some embodiments, when the training loss of the loss function is convergent, for example, the training loss keeps a constant, the processing device 120 may terminate the training, and determine the current model as the optimal predictive model. In some embodiments, when the number of training rounds (or counts of iterations) is equal to a maximum value (e.g., 50, 100, 150, etc.), the processing device 120 may also terminate the training, and determine the current model as the optimal predictive model. It should be noted that an accuracy of the predictive model may be equal to or greater than an accuracy threshold (e.g., 80%, 85%, 90%, etc.). The accuracy of the predictive model may be measured by verifying a test set. The test set is similar to the training set. The test set may include labeled historical preheating data of the immobilizing devices corresponding to a plurality of subjects and the characteristics of the plurality of subjects. In the verification of the test set, if the accuracy of the predictive model is not satisfied, the processing device 120 may continue to train the model by adjusting parameters of the predictive model until the accuracy is equal to or greater than the accuracy threshold.

Figure 9:
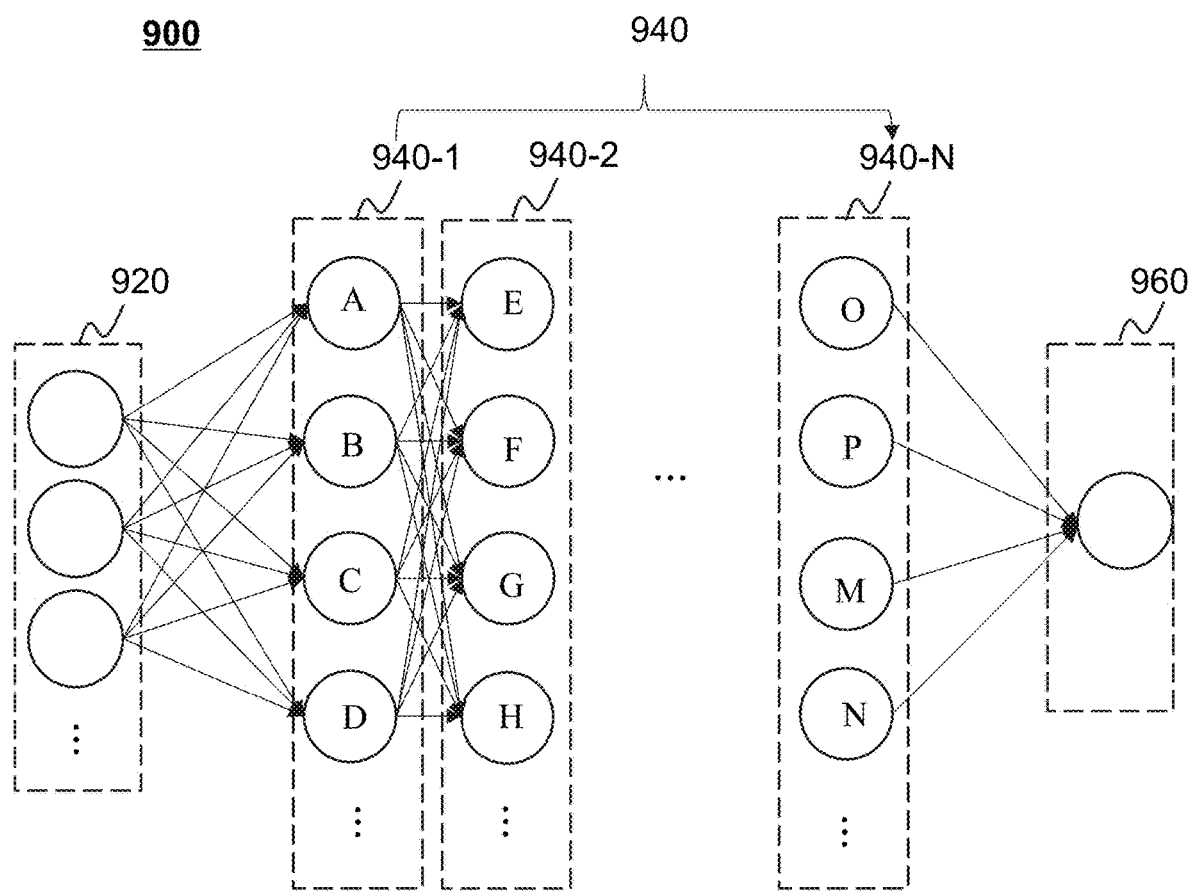
FIG. 9 is a schematic diagram illustrating an exemplary convolutional neural network (CNN) model according to some embodiments of the present disclosure.

Merely for illustration, the initial model may be the CNN model. FIG. 9 illustrates an exemplary convolutional neural network (CNN) model according to some embodiments of the present disclosure. As shown in FIG. 9, CNN model 900 may include an input layer 920, hidden layers 940, and an output layer 960. The multiple hidden layers 940 may include one or more convolutional layers, one or more Rectified Linear Units layers (ReLU layers), one or more pooling layers, one or more fully connected layers, or the like, or a combination thereof.

As used herein, a layer of a model may refer to an algorithm or a function for processing input data of the layer. Different layers may perform different kinds of processing on their respective input. A successive layer may use output data from a previous layer of the successive layer as input data. In some embodiments, each of the layer may include one or more nodes (e.g., neural units). In some embodiments, each node may be connected to one or more nodes in a previous layer. The number of nodes in each layer may be the same or different. In some embodiments, each node may correspond to an activation function. As used herein, an activation function of a node may define an output of the node given an input or a set of inputs. The activation function may include a sigmoid function, a tanh function, a ReLU function, an ELU function, a PReLU function, or the like, or any combination thereof.

In some embodiments, the plurality of nodes may be configured to process input vector(s). In a neural network model, a node may refer to a neural unit. For example, a neural unit may output a value according to Equation (1) as follows:

$$f_{output} = f(\Sigma_i w_i x_i + b) \quad (1),$$

where $f_{output}$ denotes an output value of a neural unit, $f(\cdot)$ denotes an activation function, $w_i$ demotes a weight corresponding to an element of an input vector, $x_i$ denotes an element of an input vector, and b denotes a bias term corresponding to the input vector. The weights and the bias terms may be parameters of the CNN model. In some embodiments, the weights and the bias terms may be iteratively updated based on the SGD algorithm.

For illustration purposes, as shown in FIG. 9, exemplary hidden layers 940 of the CNN model 900, including a convolutional layer 940-1, a pooling layer 940-2, and a fully connected layer 940-N, are illustrated. As described in connection with process 800, the processing device 120 may acquire the training set as an input of the input layer 920. The input training data may be in the form of a vector. The convolutional layer 940-1 may include a plurality of convolutional kernels (e.g., A, B, C, and D). For example, the number of the plurality of convolutional kernels may be in a range from 16 to 64, for example, 32. The plurality of convolutional kernels may be used to perform convolutional operation for outputs from a previous layer (e.g., the input layer 920). In some embodiments, each of the plurality of convolutional kernels may filter a portion (e.g., a region) of the input vector to achieve data dimensionality reduction.

The pooling layer 940-2 may take the output of the convolutional layer 940-1 as an input. The pooling layer 940-2 may include a plurality of pooling nodes (e.g., E, F, G, and H). Each of the plurality of pooling nodes may perform a pooling operation for its inputs, such as a max pooling, an average pooling or L2-norm pooling. For example, the plurality of pooling nodes may be used to sample the output of the convolutional layer 940-1, and thus may reduce the computational load of data processing and increase the speed of data processing of the radiation therapy system 100.

The fully connected layer 940-N may include a plurality of neural units (e.g., O, P, M, and N). The plurality of neural units in the fully connected layer 940-N may have full connections to all activations in the previous layer, and output a vector. The output layer 960 may determine an output based on the output vector of the fully connected layer 940-N and the corresponding weights and bias terms obtained in the fully connected layer 940-N. The output value may be designated as a reference of the preheating temperature of the immobilizing device.

In some embodiments, the processing device 120 may get access to multiple processing units, such as GPUs, in the radiation therapy system 100. The multiple processing units may perform parallel processing in some layers of the CNN model. The parallel processing may be performed in such a manner that the calculations of different nodes in a layer of the CNN model may be assigned to two or more processing units. For example, one GPU may run the calculations corresponding to kernels A and B, and the other GPU(s) may run the calculations corresponding to kernels C and D in the convolutional layer 940-1. Similarly, the calculations corresponding to different nodes in other type of layers in the CNN model may be performed in parallel by the multiple GPUs.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation therapy system comprising:
a therapeutic apparatus, wherein the therapeutic apparatus includes a radiation source for directing therapeutic radiation to at least one portion of a region of interest (ROI) of one of multiple subjects, immobilizing devices one of which is used for immobilizing the subject after being molded around the subject to form a molded immobilizing device;
at least one storage device storing executable instructions; and
at least one processing device in communication with the therapeutic apparatus and the at least one storage device, when executing the executable instructions, the at least one processing device causing the radiation therapy system to:
obtain a radiation therapy planning protocol of the subject;
obtain a preheated immobilizing device by preheating the molded immobilizing device by a preheating system before the immobilizing device for immobilizing the subject is installed in the therapeutic apparatus in response to a request for heating the molded immobilizing device, wherein the molded immobilizing device keeps a shape molded during the preheating and the radiation therapy treatment of the subject;
wherein the preheated immobilizing device used for immobilizing the subject is mounted on a supporting platform of a treatment table of the therapeutic apparatus before a subject's turn for receiving the radiation therapy treatment; and
control the therapeutic apparatus to apply the therapeutic radiation to the at least one portion of the ROI according to the radiation therapy planning protocol.

2. The system of claim 1, wherein one of the immobilizing-devices includes a vacuum cushion, the vacuum cushion further including:
a shell installed with a valve that is connectable to a vacuum source;
a heating element attached to an inner side of the shell;
an electrical circuit electrically connected to the heating element, wherein the electrical circuit supplies a heating voltage to the heating element for preheating the vacuum cushion; and
a filler material contained within a region defined by the shell.

3. The system of claim 2, wherein the heating element includes a flexible heating film.

4. The system of claim 3, wherein the flexible heating film includes a Carbon fiber heating film or a Graphene heating film.

5. The system of claim 2, wherein the one of the immobilizing devices further includes a temperature sensor for detecting a heating temperature of the vacuum cushion.

6. The system of claim 5, wherein the electrical circuit is connected to a temperature controller for control of the heating temperature of the vacuum cushion, and the temperature controller has a temperature memory function for recording a previously configured preferable temperature for the subject, and directly configures the recorded preferable temperature as the heating temperature of the vacuum cushion.

7. The system of claim 1, wherein the at least one processing device causes the radiation therapy system to:
preheat the molded immobilizing device according to a predictive model that processes characteristics information of the subject; wherein the characteristics information is determined based on a radiation therapy planning protocol regarding the subject, and the characteristics information of the subject includes at least one of a height, a weight, an age, a gender, a lesion, and radiation parameters.

8. The system of claim 7, wherein the characteristics information of the subject is obtained according to operations including:
obtaining a preheating request; and
obtaining the characteristics information of the subject by parsing the preheating request, the preheating request including the characteristics information of the subject and an identifier regarding the immobilizing devices.

9. The system of claim 1, wherein
the system is further configured to preheat the molded immobilizing device by the preheating system according to a predictive model that processes characteristics information of the subject;
and the predictive model is determined according to operations including:
generating, based on historical preheating data of one or more sample immobilizing devices corresponding to a plurality of sample subjects and characteristics of the plurality of sample subjects, the predictive model by training an initial model; wherein to generate the predictive model, the system is further configured to:
obtain, from a database, a set of training data including labeled historical preheating data of the one or more sample immobilizing devices corresponding to the plurality of sample subjects and the characteristics of the plurality of sample subjects; and
train the initial model based on the training data, the training including:
updating parameters of the initial model by minimizing a loss function of the initial model; and
determine the predictive model if a value of the loss function is less than or equal to a threshold.

10. The system of claim 1, wherein the at least one processing device is further configured to cause the system to generate a control signal according to operations including:
reconstructing, based on acquired image data, an image associated with the at least one portion of the ROI;
determining, based on the reconstructed image, a parameter associated with a size of the at least one portion of the ROI; and
generating, based on the parameter associated with the size of the at least one portion of the ROI, the control signal.

11. The system of claim 1, wherein the immobilizing devices one to one correspond to the subject.

12. The system of claim 1, wherein when the immobilizing-devices are heated to a specific temperature less than a recommended heating temperature, the therapeutic apparatus is configured to prepare a preliminary workflow before the immobilizing component is preheated to the recommended heating temperature.

13. The system of claim 1, wherein the preheating system is used to preheat the immobilizing devices in advance in response to preheating requests from the patients.

14. A therapeutic apparatus comprising:
an imaging device configured to acquire image data with respect to a region of interest (ROI) of a subject;
a radiation therapy device configured to apply therapeutic radiation to at least one portion of the ROI in response to a control signal, wherein the control signal is generated according to the acquired image data; and
immobilizing devices one of which is configured to immobilize the subject after being molded around the subject to form a molded immobilizing-device, wherein the molded immobilizing device is preheated to a certain temperature to be a preheated immobilizing device before the therapeutic radiation by a preheating system before the immobilizing devices are installed in the therapeutic apparatus in response to a request for heating the molded immobilizing device, the preheated immobilizing device is mounted on a supporting platform of a treatment table of the therapeutic apparatus before a subject's turn for receiving the radiation therapy treatment, and the molded immobilizing device keeps a shape molded during the preheating and the radiation therapy treatment of the subject.

15. The therapeutic apparatus of claim 14, wherein one of the immobilizing devices includes a vacuum cushion, the vacuum cushion further including:

a shell installed with a valve that is connectable to a vacuum source;

a heating element attached to an inner side of the shell;

an electrical circuit electrically connected to the heating element, wherein the electrical circuit supplies a heating voltage to the heating element for preheating the vacuum cushion; and a filler material contained within a region defined by the shell.

16. The therapeutic apparatus of claim 15, wherein the heating element includes a flexible heating film that does not interfere with a radiation beam generated by a radiation source.

17. The therapeutic apparatus of claim 15, wherein one of the immobilizing devices further includes a temperature sensor for detecting a heating temperature of the vacuum cushion.

18. The therapeutic apparatus of claim 14, wherein the control signal is generated according to operations including:

reconstructing an image regarding the at least one portion of the ROI based on the acquired image data;

determining a parameter associated with a size of the at least one portion of the ROI based on the reconstructed image; and generating the control signal according to the parameter associated with the size of the at least one portion of the ROI.

* * * * *